(12) United States Patent
Terzic et al.

(10) Patent No.: US 11,209,341 B2
(45) Date of Patent: Dec. 28, 2021

(54) TOOL FOR EXTRACTING SOIL PLUGS FOR ANALYTICAL TESTING

(71) Applicant: 1936100 Ontario Inc., Baden (CA)

(72) Inventors: Hrvoje Terzic, Waterloo (CA); Chris Morton, Baden (CA); Gina Ruttan, Baden (CA)

(73) Assignee: 1936100 Ontario Inc., Baden (CA)

( * ) Notice: Subject to any disclaimer, the term of this patent is extended or adjusted under 35 U.S.C. 154(b) by 31 days.

(21) Appl. No.: 16/885,204

(22) Filed: May 27, 2020

(65) Prior Publication Data

US 2020/0378872 A1 Dec. 3, 2020

Related U.S. Application Data

(60) Provisional application No. 62/853,406, filed on May 28, 2019.

(51) Int. Cl.
| | |
|---|---|
| *G01N 1/08* | (2006.01) |
| *G01N 33/24* | (2006.01) |
| *E21B 25/00* | (2006.01) |
| *E21B 49/02* | (2006.01) |

(52) U.S. Cl.
CPC ............ *G01N 1/08* (2013.01); *G01N 33/24* (2013.01); *E21B 25/005* (2013.01); *E21B 49/02* (2013.01)

(58) Field of Classification Search
CPC .. G01N 1/02; G01N 1/04; G01N 1/08; G01N 33/24; E21B 25/00; E21B 25/005; E21B 49/02; E02D 1/025; E02D 1/04
See application file for complete search history.

(56) References Cited

U.S. PATENT DOCUMENTS

| | | |
|---|---|---|
| 3,326,049 A | 6/1967 | Eley |
| 5,706,904 A | 1/1998 | Turriff et al. |
| 6,125,948 A | 10/2000 | David et al. |
| 6,176,326 B1 | 1/2001 | David et al. |

*Primary Examiner* — Benjamin R Schmitt
(74) *Attorney, Agent, or Firm* — Bereskin & Parr LLP

(57) ABSTRACT

A soil sampler including an elongated barrel having an inner surface defining a piston chamber with open top and bottom ends; a plunger shaped to be slidably received in the chamber and including a piston shaped to frictionally engage the inner surface of the chamber and a plunger cap joined to the piston by a shaft; and at least one longitudinally extending rib projecting inwardly from the inner surface of the chamber and having a bottom surface spaced from the open bottom end to block the piston from moving further towards the open top end, and wherein the plunger cap has at least one notch shaped to receive the at least one rib. A method of assembling a soil sampler includes aligning a notch of a plunger cap of a plunger with a rib in a piston chamber and passing the plunger cap through the chamber.

15 Claims, 7 Drawing Sheets

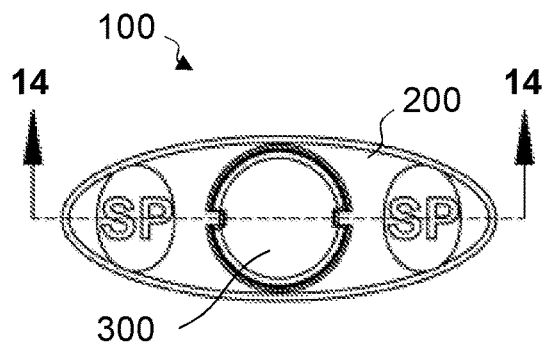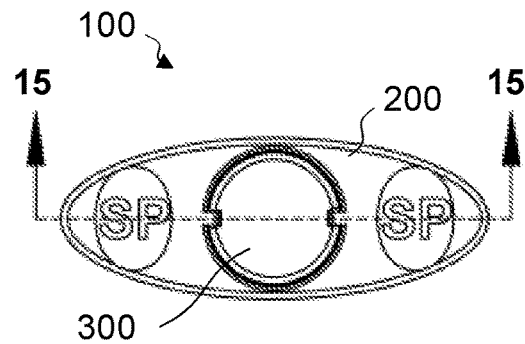
FIG. 12  FIG. 13
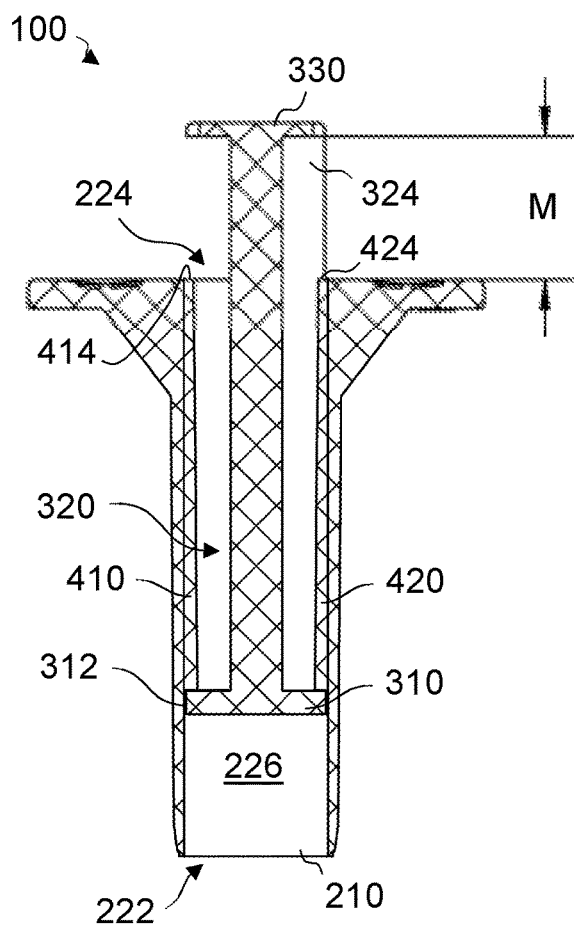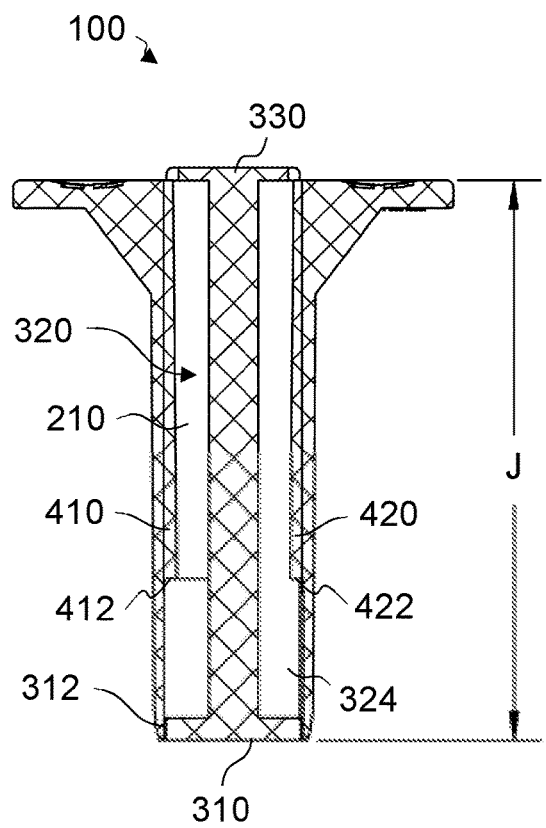
FIG. 14  FIG. 15

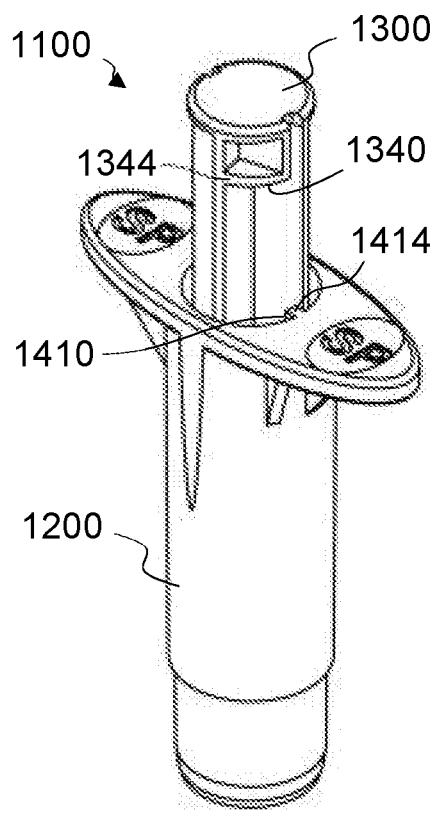
FIG. 16
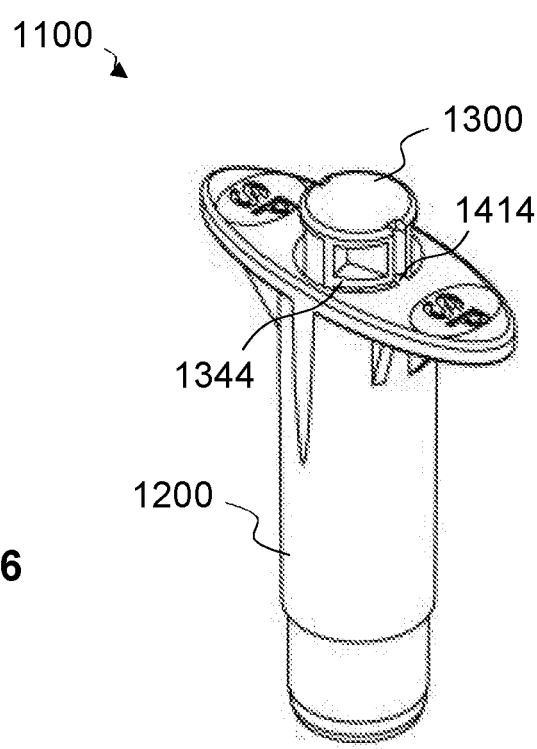
FIG. 17
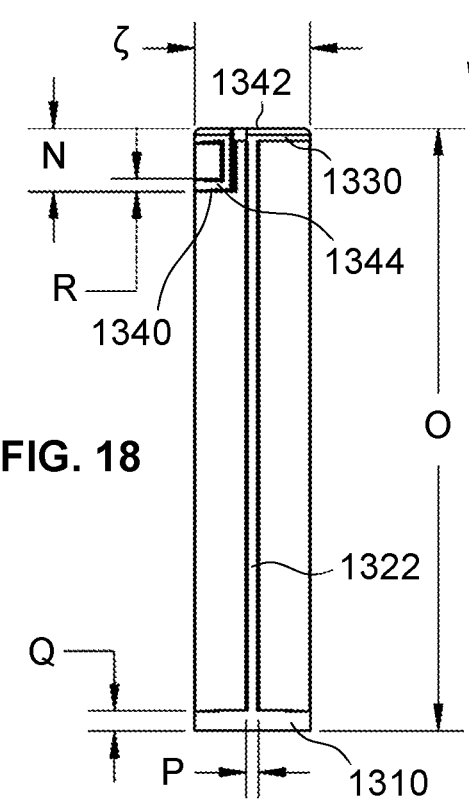
FIG. 18
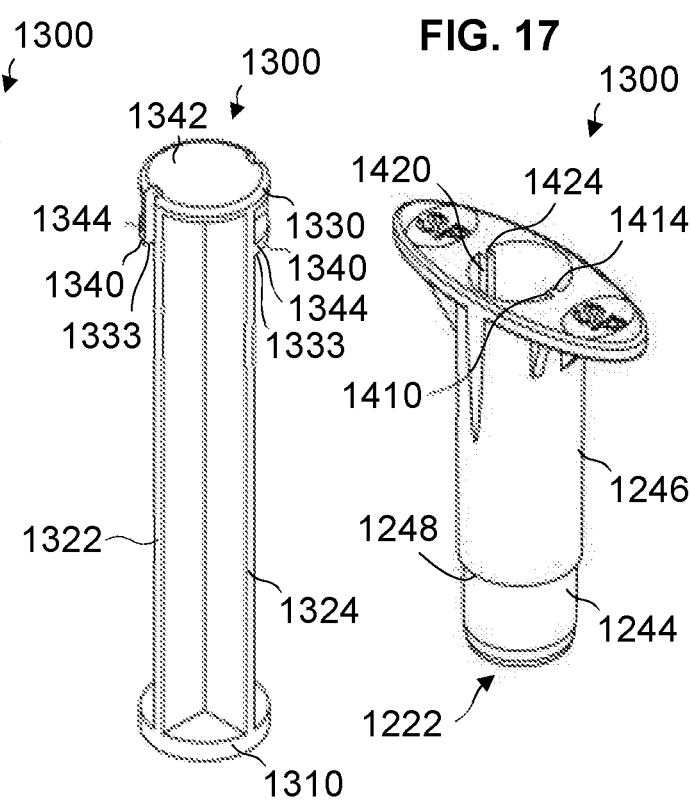
FIG. 19
FIG. 20

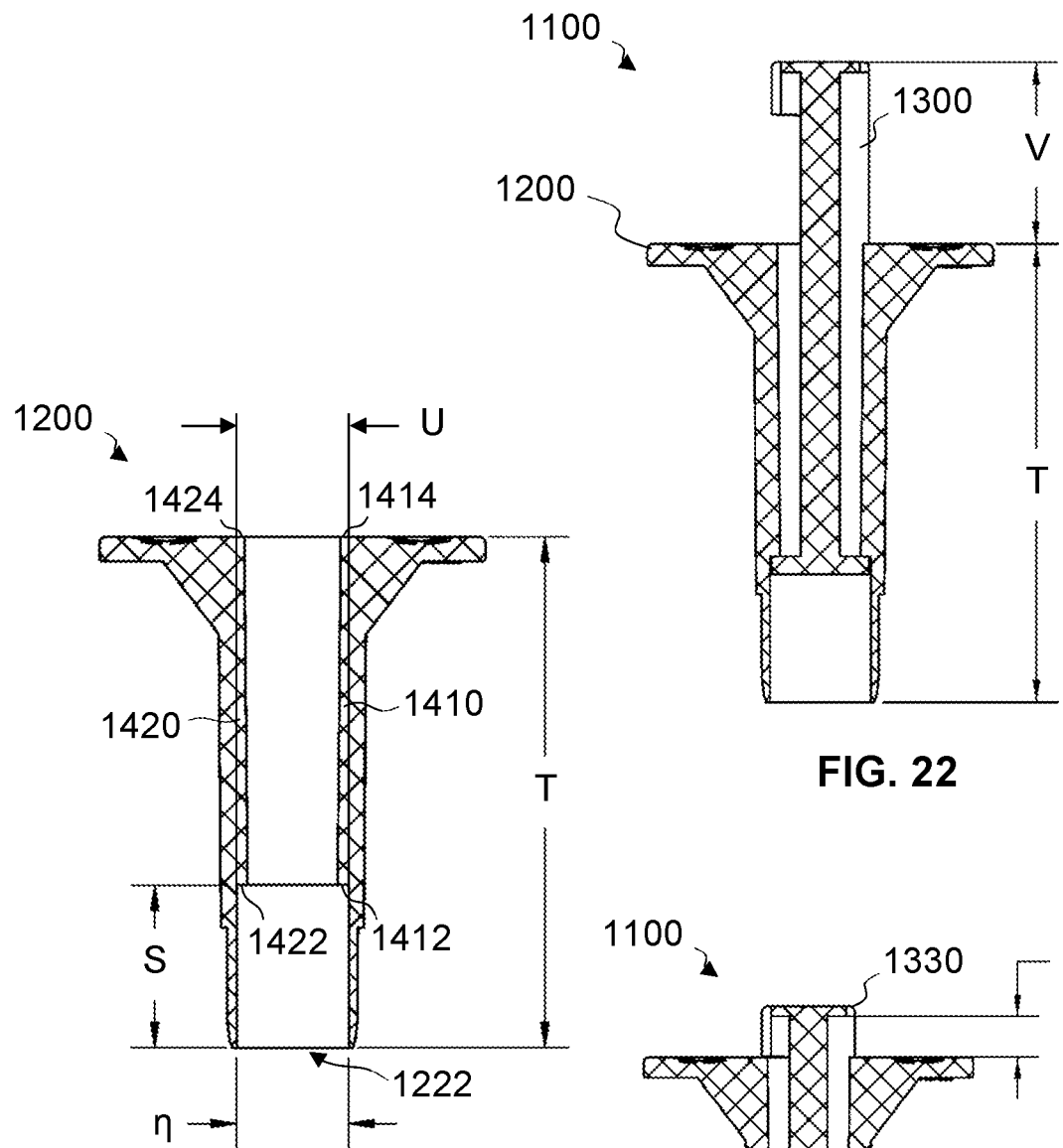

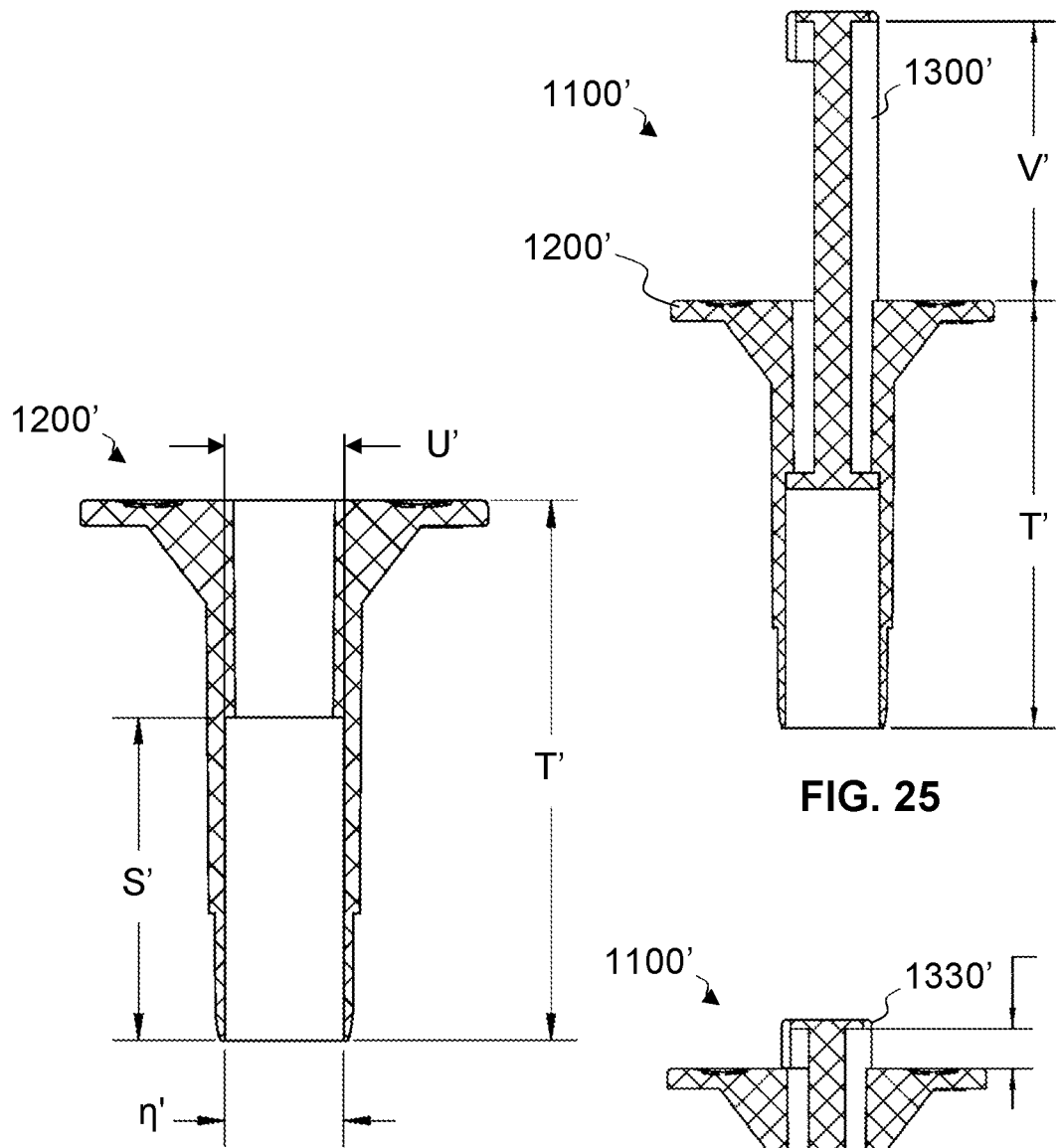

TOOL FOR EXTRACTING SOIL PLUGS FOR ANALYTICAL TESTING

TECHNICAL FIELD

The disclosure relates to soil sampling, and particularly to a tool for extracting soil plugs for analytical testing.

BACKGROUND

A variety of soil sampling devices have been developed and disclosed.

U.S. Pat. No. 5,706,904 discloses a soil-sampling tool having a barrel with a distal end for insertion into soil, and a plunger mounted for movement in the barrel. The plunger includes a soil-contact surface spaced from the distal end by a dimension when the barrel is filled with a soil sample having a volume. The improved tool includes a locking mechanism setting the dimension equal to a reference dimension, thereby establishing the volume of the soil sample to be equal to a predetermined or reference volume.

U.S. Pat. No. 6,125,948 discloses a soil sampling device providing a single use unit with an integrally molded plunger. The soil sampling device includes a cylindrical body having a first chamber and a second chamber, with each chamber comprising a cylindrical wall having a longitudinal axis and an end wall. An open end of each chamber defines a mouth which is adaped for inserting into soil. A piston may be positioned within each chamber, and the end walls include a projecting member extending outwardly therefrom which defines a plunger. The end wall includes a reduced cross-section around the projecting member and is adapted to break when a force is applied to the projecting member to thereby permit the plunger enter into the body and thereby push the piston along the longitudinal axis to expel a sample of soil collected in the body.

U.S. Pat. No. 6,176,326 discloses a soil sampling measuring device for collecting and measuring samples of soil for testing the volatile organic compounds in the soil. The soil sampling device includes a tactile indication of the volume of soil collected in the sampling device so that a person using the soil sampling device can determine when a desired volume of soil is collected in the soil sampling device without the need to refer to a visual scale. The soil sampling device includes a barrel and a plunger in the barrel, with at least one of the plunger and the barrel adapted to provide a change of resistance between the plunger and the barrel when the plunger is extended or retracted through the barrel which provides a tactile indication to the user of the soil sampling device that the plunger has reached a desired volume within the barrel. For example, the barrel of the device may include a rib or groove which respectively increases or decreases the friction between the plunger and the inner surface of the barrel.

However, these prior art devices tend to be difficult to manufacture, assemble, or employ.

SUMMARY

In a first aspect, some embodiments of the invention provide a soil sampler, comprising an elongated barrel having an inner surface defining a piston chamber, the piston chamber having an open bottom end and an open top end; a plunger shaped to be slidably received in the piston chamber, the plunger including a piston shaped to frictionally engage the inner surface of the piston chamber, a plunger cap shaped to cover at least a part of the open top end of the piston chamber, and a shaft connecting the piston to the plunger cap; and at least one longitudinally extending rib projecting inwardly from the inner surface of the piston chamber, the at least one longitudinally extending rib having a bottom surface spaced from the open bottom end by a predetermined distance, the bottom surface being shaped to block the piston from moving further towards the open top end, and wherein the plunger cap has at least one notch shaped to receive the at least one longitudinally extending rib to allow the plunger cap to move within the piston chamber between the open bottom end and the open top end guided by the at least one longitudinally extending rib.

In some embodiments, the piston chamber is a cylindrical chamber and the piston is a disc-shaped piston having a flat bottom surface.

The at least one longitudinally extending rib may comprise at least two longitudinally extending ribs and the at least one notch comprises at least two notches.

The at least two longitudinally extending ribs may be diametrically opposite to one another across the piston chamber, and the plunger cap is a disc-shaped cap and the at least two notches are a pair of notches diametrically opposite to one another.

The shaft may be a cross-shaped pair of cross members.

Each notch of the pair of notches may be positioned adjacent a first cross member of the cross-shaped pair of cross members.

The soil sampler may further comprise a handle flange secured to the barrel adjacent the open top end of the piston chamber.

An outer surface of the barrel may taper towards the inner surface at the open bottom end to form a beveled insertion edge.

The barrel may include a recessed lower portion adjacent to the open bottom end and extending to the open bottom end, the recessed lower portion having a smaller diameter than a main body of the barrel such that an annular shoulder is formed between the main body and the recessed lower portion to sit on a brim of the vial.

The rim of the plunger cap may form at least one blocking edge and the at least one longitudinally extending rib may have a top surface opposite the bottom surface, the blocking edge portion engaging with the top surface and thereby prevent further downward movement of the plunger within the barrel when the piston is rotated so as to dis-align the at least one notch and the at least one longitudinally extending rib.

The plunger may include blocking edge portions between the notches, the blocking edge portions engaging with the top surfaces of the ribs and thereby preventing further downward movement of the plunger within the barrel when the piston is rotated so as to dis-align the notches and the ribs.

The blocking edge portions may comprise portions of the rim of the plunger cap between the notches.

The blocking edge portions may comprise offset blocking edge portions that are offset below the rim of the plunger cap, the offset blocking edge portions maintaining the plunger cap in a partially raised position when the piston is rotated so as to dis-align the notches with the ribs such that the offset blocking edge portion engages an upper surface of the ribs.

In a second aspect, some embodiments of the invention provide a method of assembling a soil sampler, comprising receiving an elongated barrel having an inner surface defining a piston chamber having an open bottom end and an open top end, the barrel including at least one longitudinally extending rib projecting into the piston chamber from the inner surface and having a bottom surface spaced from the open bottom end by a predetermined distance, the bottom surface being shaped to block a piston from moving further towards the open top end; receiving a plunger having the piston shaped to frictionally engage the inner surface of the piston chamber and having a plunger cap joined to the piston by a shaft, the plunger cap shaped to cover at least a part of the open top end of the piston chamber and having at least one notch shaped to receive the at least one longitudinally extending rib to allow the plunger cap to move within the piston chamber between the open bottom end and the open top end guided by the at least one longitudinally extending rib; aligning the at least one notch with the at least one longitudinally extending rib; and passing the plunger cap through the chamber from the open bottom end and out the open top end to draw the piston into the piston chamber adjacent the open bottom end.

In some embodiments, the method further comprises following passing the plunger cap through the chamber, rotating the plunger cap along a longitudinal axis of the soil sampling device to disalign the at least one notch and the at least one longitudinally extending rib to prevent the plunger cap from being pushed back through the piston chamber.

BRIEF DESCRIPTION OF THE DRAWINGS

The drawings included herewith are for illustrating various examples of systems, methods, and apparatus of the present specification. In the drawings:

FIG. 12 is a top plan view of the soil sampling device of FIG. 1;

FIG. 13 is a top plan view of the soil sampling device of FIG. 2;

FIG. 14 is a cross sectional view of the soil sampling device of FIG. 1, taken along line 14-14 of FIG. 12;

FIG. 15 is a cross sectional view of the soil sampling device of FIG. 2, taken along line 15-15 of FIG. 13;

FIG. 16 is a top perspective view of a soil sampling device in accordance with a second embodiment, with a plunger in a raised position;

FIG. 17 is a top perspective view of the soil sampling device of FIG. 16, with the plunger in a depressed position;

FIG. 18 is a side elevation view of the plunger of FIG. 16;

FIG. 19 is a top perspective view of the plunger of FIG. 16;

FIG. 20 is a top perspective view of a barrel of the soil sampling device of FIG. 16;

FIG. 21 is a cross sectional view of the barrel of FIG. 20;

FIG. 22 is a cross sectional view of the soil sampling device of FIG. 16, with the plunger in the raised position;

FIG. 23 is a cross sectional view of the soil sampling device of FIG. 16, with the plunger in the depressed position;

FIG. 24 is a cross sectional view of a barrel in accordance with a third embodiment;

FIG. 25 is a cross sectional view of a soil sampling device incorporating the barrel of FIG. 24, with a plunger in a raised position; and FIG. 26 is a cross sectional view of the soil sampling device of FIG. 25, with the plunger in a depressed position.

DETAILED DESCRIPTION

Various systems, methods and apparatus will be described below. No embodiment described below limits any claimed embodiment and any claimed embodiment may cover systems, methods and/or apparatus that differ from those described below. The claimed embodiments are not limited to systems, methods and apparatus having all of the features of any one systems, methods and apparatus described below or to features common to multiple or all described below.

Numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments generally described herein.

Figure 1:
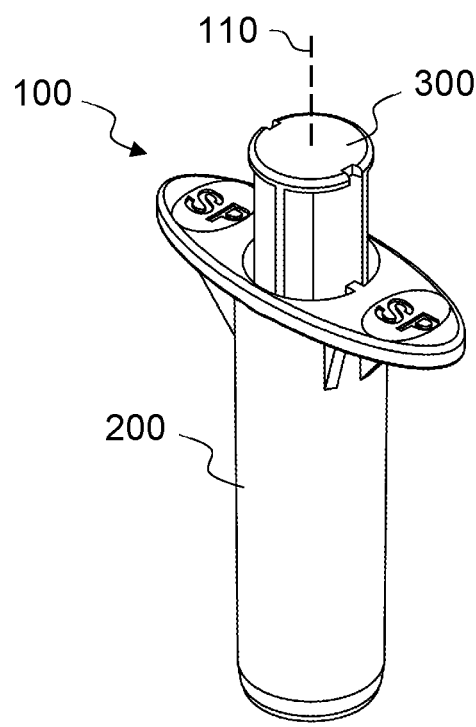
FIG. 1 is a top perspective view of a soil sampling device in accordance with a first embodiment, with a plunger in a raised position.
Figure 2:
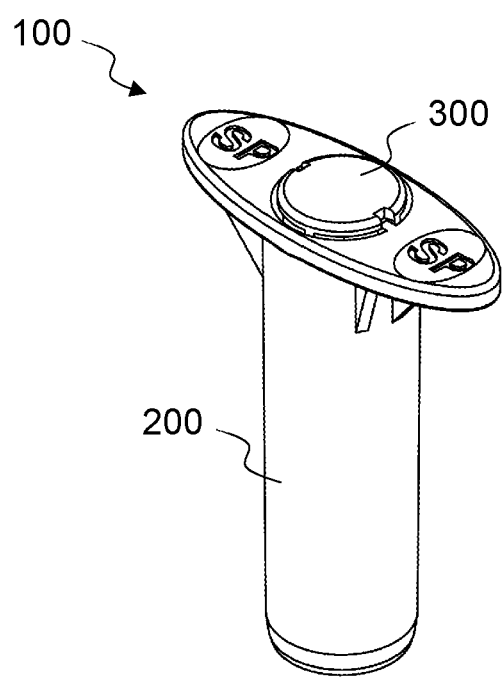
FIG. 2 is a top perspective view of the soil sampling device of FIG. 1, with the plunger in a depressed position.

A soil sampling device is depicted in FIG. 1. Soil sampling device 100 has a longitudinal axis 110 and includes a barrel 200 and a plunger 300. Barrel 200 is adapted to be driven into a volume of soil to receive a soil sample within barrel 200. Plunger 300 is received in barrel 200 and is adapted for use in ejecting a soil sample within barrel 200 by depressing plunger 300 into barrel 200. Soil sampling device 100 is depicted in FIG. 1 with plunger 300 received in barrel 200 in a raised position. Soil sampling device 100 is depicted in FIG. 2 with plunger 300 received in barrel 200 in a depressed position. Barrel 200 is depicted in FIG. 3 and plunger 300 is depicted in FIG. 4.

Soil sampling device 100 is provided as a hand held device for use in extracting a soil sample, such as a soil plug. For example, a soil sample having a predetermined volume may be required for analytical testing. To acquire the soil sample, barrel 200 with plunger 300 received therein may be driven into a volume of soil to acquire the soil sample within the barrel 200, and then plunger 300 may be depressed to expel the predetermined volume of soil into a vial to be brought to a lab for testing.

Figure 3:
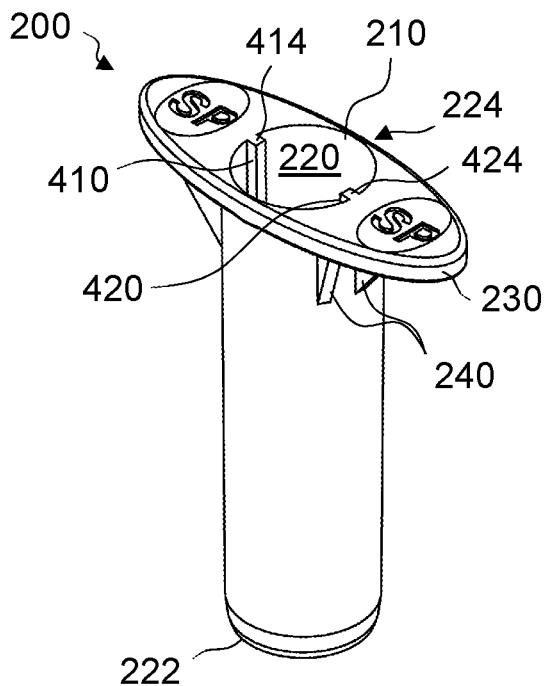
FIG. 3 is a top perspective view of a barrel of the soil sampling device of FIG. 1.
Figure 4:
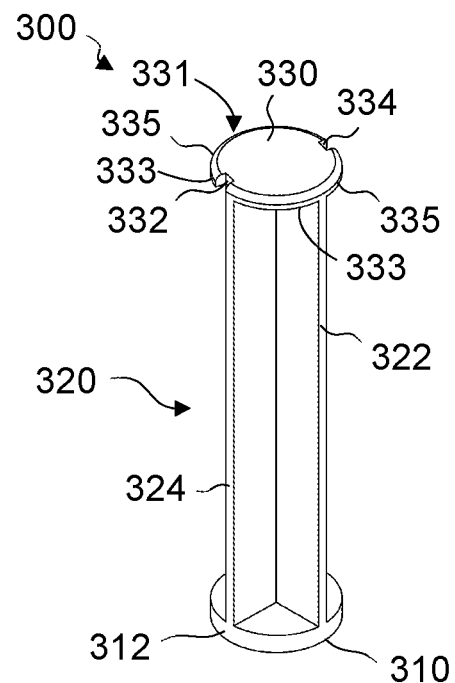
FIG. 4 is a top perspective view of the plunger of the soil sampling device of FIG. 1.

As depicted in FIG. 3, barrel 200 has an inner surface 210 defining a piston chamber 220. Piston chamber 220 has an open bottom end 222 and an open top end 224 opposite open bottom end 222.

Barrel 200 also includes a handle flange 230 for use in manipulating the barrel 200. Handle flange 230 is located adjacent the open top end 224 to allow a user to grip handle flange 230 when driving open bottom end 222 into a volume of soil. Handle flange 230 extends out perpendicular to the main body of barrel 200.

Figure 5:
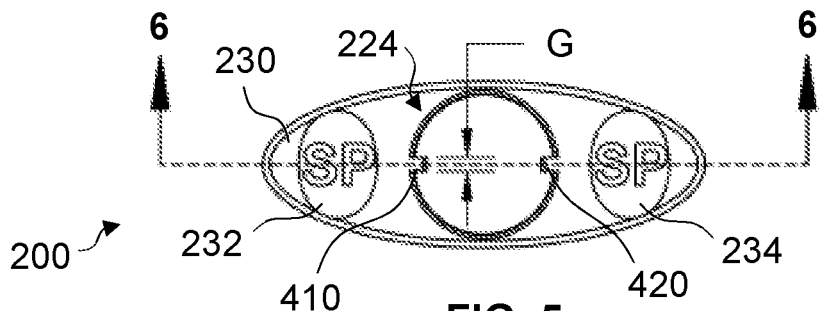
FIG. 5 is a top plan view of the barrel of FIG. 3.
Figure 8:
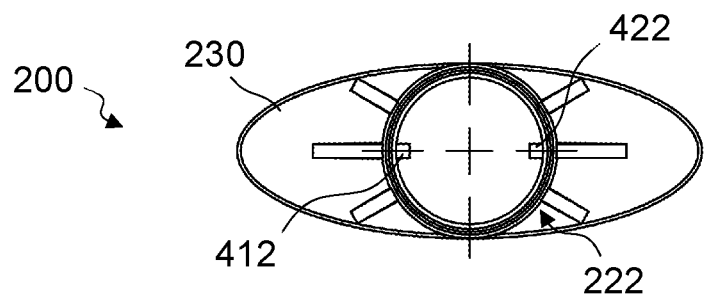
FIG. 8 is a bottom plan view of the barrel of FIG. 3.

As shown in the top view of barrel 200 in FIG. 5, handle flange 230 has first and second finger indentations 232 and 234 for receiving the fingers of a user when the user is driving the soil sampling device 100 downward. Handle flange 230 is also a convenient location for displaying information, such as logos or other information. As shown, each of finger indentations 232 and 234 may be marked with a logo. The underside of handle flange 230, shown particularly in FIG. 8, may also be marked, such as with a product information message.

Barrel 200 includes a pair of longitudinally extending ribs 410 and 420, visible in perspective in FIG. 3. Ribs 410 and 420 project into piston chamber 220 from inner surface 210. As shown particularly in FIG. 6, ribs 410 and 420, extend generally parallel to longitudinal axis 110, but may be angled relative to one another by a draft angle β, such as by an angle of 1°. Ribs 410 and 420 are formed integrally with a sidewall of barrel 200, and are diametrically opposite to one another across piston chamber 220.

Figure 6:
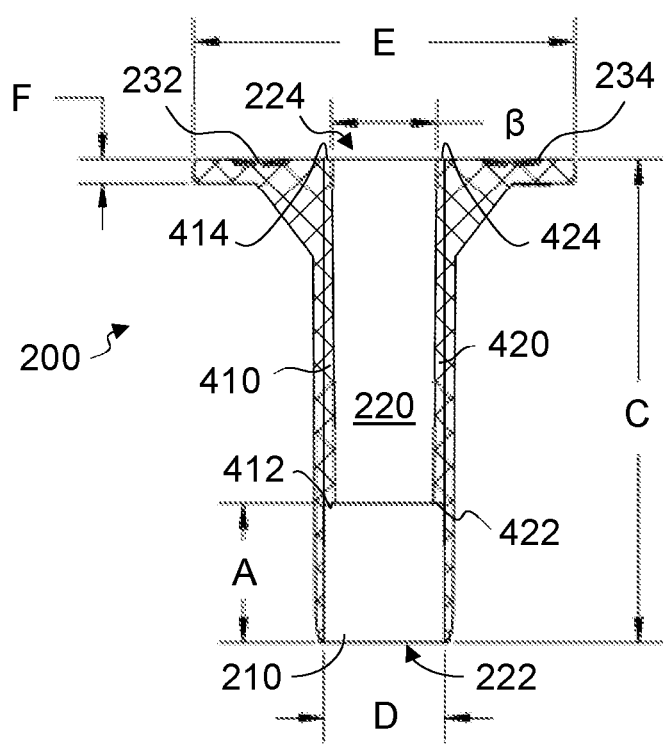
FIG. 6 is a cross sectional view of the barrel of FIG. 3, taken along line 6-6 of FIG. 5.

As shown particularly in FIG. 6, each of ribs 410 and 420 extends from open top end 224 to a distance A from open bottom end 222. Each of ribs 410 and 420 forms a bottom surface 412 and 422 directed towards the open bottom end 222. The bottom surfaces 412 and 422 are provided to stop the upward travel of the piston 310 through chamber 220 at a predetermined point. Each of ribs 410 and 420 also forms a top surface 414 and 424 directed towards the open top end 224. The top surfaces 414 and 424 are provided to stop the downward travel of the plunger cap 330 through chamber 220, when the plunger is rotated relative to the barrel 200 as described below. Ribs 410 and 420 also increase the structural strength of barrel 200, and extend in the direction in which pressure is expected to be applied to the barrel 200. In some embodiments, the thickness of a sidewall of a barrel may be reduced in areas were ribs provide structural support.

Figure 7:
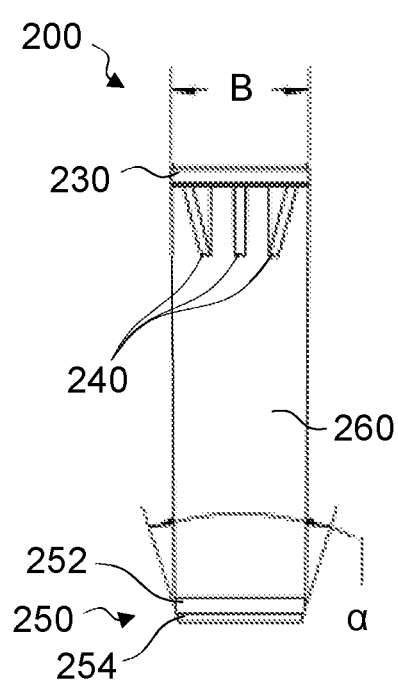
FIG. 7 is a right side elevation view of the barrel of FIG. 3.

As shown particularly in FIG. 7, barrel 200 also includes support struts 240 and a beveled insertion edge 250. Struts 240 extend from an underside of handle flange 230 to the main body of barrel 200, and are provided to support handle flange 230. Beveled insertion edge 250 is a chamfered edge formed by a truncated tapering of outer surface 260 of barrel 200 towards inner surface 210 adjacent open bottom end 222. Insertion edge 250 includes a first included surface 252 and a second inclined surface 254.

As shown particularly in FIG. 7, barrel 200 is dimensioned for use with standard sized vials. Barrel 200 is a cylindrical barrel having an outside diameter B of 0.75 inches. First and second inclined surfaces 252 and 254 result in a reduced outside diameter near open bottom end 222. For example, second inclined surface 254 of beveled edge 250 forms an angle α of 34.4°. As a result, beveled insertion edge 250 can be inserted into many standard sized cylindrical vials while the main body of barrel 200 is sufficiently large to prevent insertion. The shape of insertion edge 250 may also assist in driving barrel 200 into a volume of soil.

Further dimensions of barrel 200 are complementary to the above-recited dimensions. As shown in FIG. 6, barrel 200 has a height C of 2.54 inches, chamber 220 has an inside diameter D of 0.632 inches, handle flange 230 has a maximum width E of 2 inches, the predetermined distance A between ribs 410 and 420 and open bottom end 222 is 0.73 inches, and the thickness F of handle flange 230 is 0.13 inches. As shown in FIG. 5 the width G of ribs 410 and 420 is 0.063 inches.

Referring now to FIG. 4, the plunger 300 comprises a disc-shaped piston 310, a disc-shaped plunger cap 330 having a rim 331, and a shaft 324 connecting piston 310 to plunger cap 330. The plunger cap 330 can be used to drive piston 310 up and down within piston chamber 220, and is shaped to cover at least a part of the open top end of the piston chamber. Piston 310 has flat top and bottom surfaces, and is shaped to frictionally engage the inner surface of the piston chamber.

In the example embodiment, shaft 320 is formed of cross-shaped cross members 322 and 234, which extend between piston 310 and plunger cap 330. Cross members extend to the periphery of each of the piston 310 and plunger cap 330.

The rim 331 of plunger cap 330 has two notches 332 and 334 therein, each of which is shaped to receive one of ribs 410 and 420. Notches 332 and 334 are diametrically opposed to one another, reflecting the positioning of ribs 410 and 420 relative to one another. Notches 332 and 334 allow plunger cap 330 to pass the ribs 410 and 420 and move through piston chamber 220 between the open bottom and top ends 222 and 224. The portions of rim 331 between the notches act as blocking edge portions 335 having bottom surfaces 333 that engage with the top surfaces 414, 424 of the ribs to stop the plunger 300 from passing further into the barrel 200 when the plunger is rotated in a manner described below.

Figure 9:
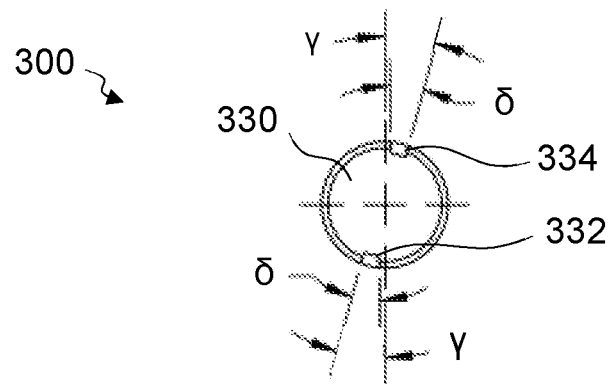
FIG. 9 is a top plan view of the plunger of FIG. 4.

Plunger 300 is dimensioned for use with barrel 200. Depicted in FIG. 9, the angle γ between adjacent strut 320 and the furthest edge of each notch 332 and 334 is 15°. The angle δ between opposite sidewalls of notches 332 and 334 is 16°.

Figure 10:
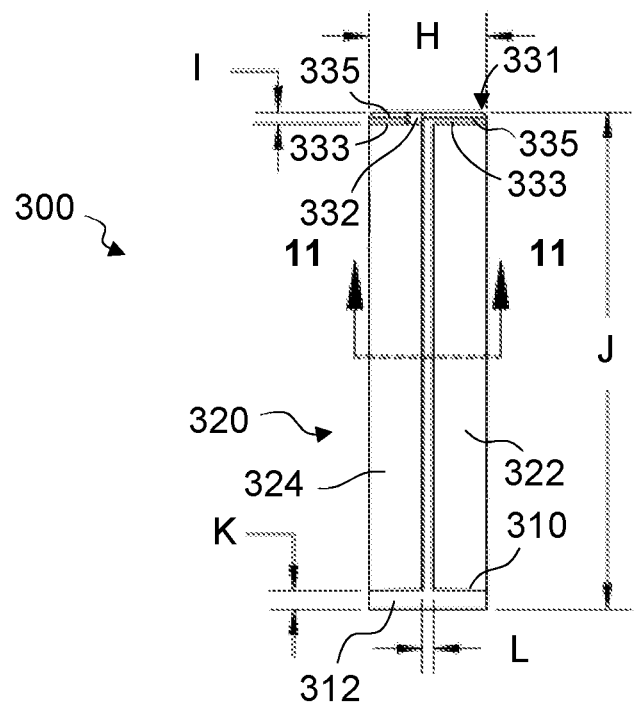
FIG. 10 is a side elevation view of the plunger of FIG. 4.
Figure 11:
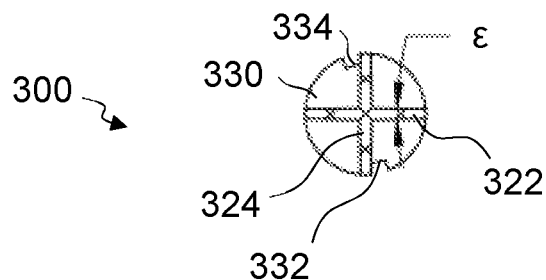
FIG. 11 is a cross sectional view of the plunger of FIG. 4, taken along line 11-11 of FIG. 10.

Further dimensions of example plunger 300 are shown in FIG. 10. The width H of plunger 300 is 0.614 inches. The thickness I of plunger cap 330 is 0.06 inches. The height J of plunger 300 is 2.60 inches. The thickness K of piston 310 is 0.097 inches. The average thickness L of cross-members 322 and 324 is 0.061 inches. As shown in FIG. 11, the draft angle ε between opposed side surfaces of each of cross-members 322 and 324 is 2°.

With reference now to FIGS. 12 to 15, when plunger 300 is received in barrel 200 it may be raised and depressed within barrel 200. Plunger 300 is in a raised position in FIGS. 12 and 14, and a lowered position in FIGS. 13 and 15.

When plunger 300 is received within barrel 200, piston 310 frictionally engages inner surface 210 along a periphery 312 of piston 310. Piston 310 separates an upper portion of piston chamber 220 from a lower portion of piston chamber 220.

In the example embodiment shown in FIG. 14, plunger cap 330 may be raised a distance M of 0.63 inches. When plunger cap 330 is raised, a sampling sub-chamber 226 of chamber 220 is formed below piston 310. In use, when barrel 200 is driven into a volume of soil, piston 310 is then driven back by the soil sample entering barrel 200. When barrel 200 is removed from the volume of soil frictional forces within barrel 200 hold the soil sample in the barrel until it is expelled by downward movement of piston 310. In some embodiments a sampling chamber has a predefined volume corresponding to standard volumes required for analytical testing, such as between 1 and 10 milliliters, between 3 and 7 milliliters, or approximately 5 milliliters.

Plunger cap 330 is able to pass through chamber 220 when notches 332 and 334 are aligned with ribs 410 and 420. However, when notches 332 and 334 of rim 331 are not aligned with ribs 410 and 420, the bottom surfaces 333 of blocking edge portions 335 of rim 331 of plunger cap 330 engage top surfaces 414 and 424 of ribs 410 and 420, shown in FIGS. 3 and 6, which prevents plunger cap 330 from passing further through chamber 220. As a result, ribs 410 and 420 may function both to limit the movement of piston 310 and to limit the movement of plunger cap 330.

Since plunger cap 330 can pass through piston chamber 220 when notches and ribs are aligned, soil sampler 100 can be produced as two discrete parts and assembled by aligning notches 332 and 334 with ribs 410 and 420 and inserting the plunger cap 320 into piston chamber 220 through open bottom end 222 and then out of piston chamber 220 through open top end 224. Plunger 300 can then be rotated or twisted around longitudinal axis 110 relative to barrel 200 to disalign notches 332 and 334 with ribs 410 and 420 so that the bottom surfaces 333 of blocking edge portions 335 hit the top surfaces 414 and 424 of ribs 410 and 420 which prevents the plunger 300 from being pushed back through piston chamber 220.

Components of a soil sampling device may be formed of a variety of materials having strength characteristics and stiffness characteristics sufficient to allow the use of the soil sampling device with a volume of soil that is to be sampled. For example, plastics or metals may be used. In some embodiments, one or more components of a soil sampling device are formed of plastic. In some embodiments, the plastic used in forming one or more components of a soil sampling device is made using a contaminant free resin. Plastic components may be formed by injection molding, and features of the components may be formed with sufficient draft in the line of draw to allow the part to be released from a mold.

The barrel 200 and plunger 300 of soil sampling device 100 are formed of a plastic. The plastic used may be a clear plastic, such as high clarity polypropylene, to ease visual assessment of the soil sampling device, such as to allow a user to gage the extent to which sampling chamber 226 is filled with a soil sample.

Referring now to FIG. 16, illustrated is another embodiment of the soil sampling device made in accordance with the present disclosure. Soil sampling device 1100 includes a barrel 1200 and a plunger 1300, the plunger 1300 shown in a raised position in FIG. 16. Soil sampling device 1100 is similar in many respects to soil sampling device 100, and like features are indicated with like reference numbers incremented by 1000.

The main difference between sample device 1100 and sampling device 110 is that in the case of device 1100 the blocking action is not provided by the blocking edge portions of the rim but rather by the offset blocking edge portions 1344 that are offset below the rim 331. Providing offset blocking edge portions between the plunger cap and the piston and offset from the top surface of the plunger maintains the plunger cap in a partially raised position when the plunger is depressed into the barrel. A partially raised plunger cap may be easier for a user to grasp, which may facilitate raising the plunger for reuse. The plunger 1300 includes at least one blocking edge 1340 directed towards the piston 1310 (FIG. 18). In the illustrated example, shown particular in FIG. 19, plunger 1300 includes two blocking edge portions 1340, each with a blocking surface 1333, to improve the balance of the soil sampling device.

Referring now to FIG. 17, the plunger 1300 is shown depressed into the barrel 1200. The at least one offset blocking edge 1340 is offset below the top surface 1342 of the plunger 1300. When the at least one offset blocking edge 1340 engages an upper surface of the rib of barrel 1200, the plunger cap 1330 stops its travel in a partially raised position. In this example, the offset blocking edge 1340 engages top edges 1414 and 1424 of ribs 1410 and 1420 (see also FIG. 20), and the plunger 1300 is prevented from being further depressed into the barrel 1200. The illustrated offset blocking edge 1340 is formed by a projection 1344, however in other examples the offset blocking edge may be the underside of a thick plunger cap offset from a top of the plunger cap by the thickness of the plunger cap.

Referring now to FIGS. 18 and 19, the offset blocking edges 1340 may be offset from the top surface 1342 of the plunger 1300 by a distance N. Distance N may be sufficient for a user to grasp the plunger 1300 to raise the plunger 1300 from the barrel 1200. For example, distance N may be more than 0.2 inches or more than 0.3 inches.

The distance N may depend on the size of the soil sampling device 1100, including the dimensions of the plunger 1300. In some examples, the plunger 1300 may have a distance N of approximately 0.30 inches and a height O of approximately 3 inches. In the illustrated example, the plunger 1300 has a distance N of 0.31 inches and a height O of 2.96 inches. The illustrated example plunger 1300 has cross members 1322 and 1324 with thicknesses P of 0.061 inches, and has a piston 1310 with a thickness Q of 0.098 inches. A thickness R of the projection 1344 of the illustrated example is 0.06 inches. The plunger 1300 may also have a draft angle $\zeta$ of approximately 0.5 degrees, such as a draft angle $\zeta$ of 0.583 degrees.

Referring now to FIG. 20, a barrel may be adapted for use with a vial, such as a vial into which a soil sample is to be deposited to be brought to a lab for testing. The barrel may be dimensioned to fit in a vial. For example, a lower portion 1244 of the barrel 1200 may be dimensioned to fit in a vial while an upper portion 1246 may be dimensioned to be sufficiently large to prevent insertion.

As described above with reference to soil sampling device 100, the barrel 200 may include a beveled insertion edge 250 at the open bottom end 122 that can be inserted into many standard sized vials, with the main body of the barrel 200 being sufficiently large to prevent insertion. However, as in the illustrated example of FIG. 20, the barrel 1200 may also include a recessed lower portion 1244 adjacent to the open bottom end 1222 and extending to the open bottom end 1222. Recessed lower portion 1244 may have a smaller diameter than a main body 1246 of the barrel 1200, forming a shoulder 1248 to rest on an upper edge of a vial.

Accordingly, the barrel 1200 can be inserted into a vial by inserting the recessed lower portion 1244 into the vial. The barrel 1200 may optionally be rested on the vial with the shoulder 1248 resting on the upper edge of the vial. For example, a user may insert the barrel 1200 of the soil sampling device 1100 into a vial and leave the barrel soil sampling device 1100 in the vial, resting on the upper edge of the vial; releasing the soil sampling device 1100 without concern that the soil sampling device 1100 will readily fall out of the vial.

Referring now to FIGS. 21 to 23, the ribs 1410 and 1420 also have bottom edges 1412 and 1422 directed towards the open bottom end 1222. As discussed above, bottom edges of ribs may be provided to stop the upwards travel of the piston 1310 through the barrel 1200 at a predetermined point. This predetermined point may be used to set the size of the soil sample that is taken by the soil sampling device 1100.

In the illustrated example, the predetermined point is a distance S from the open bottom end 1222. This distance S may be, for example, less than 1 inch, such as a distance S of 0.85 inches. The distance S may depend on the desired soil sample size and the other dimensions of the soil sampling device 1100. For example, the distance S may be 0.85 inches in a cylindrical barrel 1200 having a height T of 2.65 inches, a diameter U of 0.612 inches, and a draft angle $\eta$ of 0.583 inches. The distance S may be set to take a 5 gram soil sample.

A plunger cap 1330 of plunger 1300 is a distance V from an upper surface of the barrel 1200 when in the raised position and a distance W from the upper surface of the barrel 1200 when in the depressed position. The distance V may be approximately 1 inch and the distance W may be approximately 0.25 inches. In the illustrated example, the distance V is 1.05 inches and the distance W is 0.25 inches.

Referring now to FIGS. 24 to 26, illustrated is an example soil sampling device 1100'. Soil sampling device 1100' is a variation of the soil sampling device 1100 in which the distance S' from the open bottom end 1222' is increased to increase the size of a soil sample that can be taken by the soil sampling device 1000'. The soil sampling device 1100' has a height T' of 2.65 inches and a diameter U' of 0.612 inches, with draft angle η' of 0.583 inches. The distance S' may be greater than 1 inch or greater than 1.5 inches. For example, the distance S' may be 1.59 inches, and may be set to allow the soil sampling device 1100' to take a 10 gram soil sample.

A plunger cap 1330' of plunger 1300' is a distance V' from an upper surface of the barrel 1200 when in the raised position and a distance W' from the upper surface of the barrel 1200 when in the depressed position. The distance V' may be approximately 1.7 inch and the distance W' may be approximately 0.25 inches. In the illustrated example, the distance V' is 1.73 inches and the distance W' is 0.25 inches.

The present invention has been described here by way of example only. For example, soil sampling device 100 is described herein with specific dimensions, however in other embodiments of a soil sampling device other dimensions may be used. Various modification and variations may be made to exemplary embodiments without departing from the scope of the invention, which is limited only by the appended claims.

The invention claimed is:

1. A soil sampler, comprising:
an elongated barrel having an inner surface defining a piston chamber, the piston chamber having an open bottom end and an open top end;
a plunger shaped to be slidably received in the piston chamber, the plunger including a piston shaped to frictionally engage the inner surface of the piston chamber, a plunger cap shaped to cover at least a part of the open top end of the piston chamber, and a shaft connecting the piston to the plunger cap; and
at least one longitudinally extending rib projecting inwardly from the inner surface of the piston chamber, the at least one longitudinally extending rib having a bottom surface spaced from the open bottom end by a predetermined distance, the bottom surface being shaped to block the piston from moving further towards the open top end, and
wherein the plunger cap has at least one notch shaped to receive the at least one longitudinally extending rib to allow the plunger cap to move within the piston chamber between the open bottom end and the open top end guided by the at least one longitudinally extending rib.

2. The soil sampler of claim 1, wherein the piston chamber is a cylindrical chamber and the piston is a disc-shaped piston having a flat bottom surface.

3. The soil sampler of claim 2, wherein the at least one longitudinally extending rib comprises at least two longitudinally extending ribs and the at least one notch comprises at least two notches.

4. The soil sampler of claim 3, wherein the at least two longitudinally extending ribs are diametrically opposite to one another across the piston chamber, and the plunger cap is a disc-shaped cap and the at least two notches are a pair of notches diametrically opposite to one another.

5. The soil sampler of claim 4, wherein the shaft is a cross-shaped pair of cross members.

6. The soil sampler of claim 5, wherein each notch of the pair of notches is positioned adjacent a first cross member of the cross-shaped pair of cross members.

7. The soil sampler of claim 1, further comprising a handle flange secured to the barrel adjacent the open top end of the piston chamber.

8. The soil sampler of claim 7, wherein an outer surface of the barrel tapers towards the inner surface at the open bottom end to form a beveled insertion edge.

9. The soil sampler of claim 1, wherein the barrel includes a recessed lower portion adjacent to the open bottom end and extending to the open bottom end, the recessed lower portion having a smaller diameter than a main body of the barrel such that an annular shoulder is formed between the main body and the recessed lower portion to sit on a brim of the vial.

10. The soil sampler of claim 1, wherein the rim of the plunger cap forms at least one blocking edge and the at least one longitudinally extending rib has a top surface opposite the bottom surface, the blocking edge portion engaging with the top surface and thereby prevent further downward movement of the plunger within the barrel when the piston is rotated so as to dis-align the at least one notch and the at least one longitudinally extending rib.

11. The soil sampler of claim 10, wherein the plunger includes blocking edge portions between the notches, the blocking edge portions engaging with the top surfaces of the ribs and thereby preventing further downward movement of the plunger within the barrel when the piston is rotated so as to dis-align the notches and the ribs.

12. The soil sampler of claim 11, wherein the blocking edge portions comprise portions of the rim of the plunger cap between the notches.

13. The soil sampler of claim 11, wherein the blocking edge portions comprise offset blocking edge portions that are offset below the rim of the plunger cap, the offset blocking edge portions maintaining the plunger cap in a partially raised position when the piston is rotated so as to dis-align the notches with the ribs such that the offset blocking edge portion engages an upper surface of the ribs.

14. A method of assembling a soil sampler, comprising:
receiving an elongated barrel having an inner surface defining a piston chamber having an open bottom end and an open top end, the barrel including at least one longitudinally extending rib projecting into the piston chamber from the inner surface and having a bottom surface spaced from the open bottom end by a predetermined distance, the bottom surface being shaped to block a piston from moving further towards the open top end;
receiving a plunger having the piston shaped to frictionally engage the inner surface of the piston chamber and having a plunger cap joined to the piston by a shaft, the plunger cap shaped to cover at least a part of the open top end of the piston chamber and having at least one notch shaped to receive the at least one longitudinally extending rib to allow the plunger cap to move within the piston chamber between the open bottom end and the open top end guided by the at least one longitudinally extending rib;
aligning the at least one notch with the at least one longitudinally extending rib; and passing the plunger cap through the chamber from the open bottom end and out the open top end to draw the piston into the piston chamber adjacent the open bottom end.

15. The method of claim 14, further comprising, following passing the plunger cap through the chamber, rotating the plunger cap along a longitudinal axis of the soil sampling device to disalign the at least one notch and the at least one longitudinally extending rib to prevent the plunger cap from being pushed back through the piston chamber.

* * * * *